US010201526B2

(12) United States Patent
Edwards et al.

(10) Patent No.: US 10,201,526 B2
(45) Date of Patent: Feb. 12, 2019

(54) COMPOSITIONS AND METHODS FOR INHIBITING THE GROWTH OF NEISSERIA GONORRHOEAE

(71) Applicants: Research Institute at Nationwide Children's Hospital, Columbus, OH (US); Ohio State Innovation Foundation, Columbus, OH (US)

(72) Inventors: Jennifer Edwards, Westerville, OH (US); Alexander Zukiwski, Clarksburg, MD (US)

(73) Assignees: Research Institute at Nationwide Children's Hospital, Columbus, OH (US); Ohio State Innovation Foundation, Columbus, OH (US)

(*) Notice: Subject to any disclaimer, the term of this patent is extended or adjusted under 35 U.S.C. 154(b) by 0 days.

(21) Appl. No.: 15/276,739

(22) Filed: Sep. 26, 2016

(65) Prior Publication Data
US 2017/0087130 A1 Mar. 30, 2017

Related U.S. Application Data

(60) Provisional application No. 62/233,723, filed on Sep. 28, 2015.

(51) Int. Cl.
*A61K 31/415* (2006.01)
*A61K 31/546* (2006.01)
*A61K 31/7036* (2006.01)
*A61K 45/06* (2006.01)

(52) U.S. Cl.
CPC .......... *A61K 31/415* (2013.01); *A61K 31/546* (2013.01); *A61K 31/7036* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,037,945 B2 * | 5/2006 | Docherty ............... | A61K 31/05 514/733 |
| 7,576,116 B2 | 8/2009 | Chen | |
| 8,039,502 B2 | 10/2011 | Chen et al. | |
| 8,080,574 B2 | 12/2011 | Chen | |
| 8,541,460 B2 | 9/2013 | Chen | |
| 8,546,441 B2 | 10/2013 | Chen | |
| 9,744,156 B2 * | 8/2017 | Murthy ................ | A61K 31/415 |
| 2012/0122872 A1 | 5/2012 | Krysan et al. | |

FOREIGN PATENT DOCUMENTS

WO 2014022382 A2 2/2014

OTHER PUBLICATIONS

Golparian et al. Antimicrobial Agents and Chemotherapy. May 2012; 56(5):2739-2742. (Year: 2012).*

Booth, et al., "GRP78/BiP/HSPA5/Dna K is a universal therapeutic target for human disease," J Cell Physiol., Jul. 2015, vol. 230, No. 7, pp. 1661-1676.
International Search Report of International PCT Application No. PCT/US2016/053843 dated on Jan. 13, 2017.
Agarwal et al., "Factor H Facilitates Adherence of Neisseria gonorrhoeae to Complement Receptor 3 on Eukaryotic Cells," The Journal of Immunology, Sep. 2010, vol. 185, pp. 4344-4353.
Alvarez et al., "3-Phosphoinositide-dependent protein kinase-1/Akt signaling and inhibition in a canine prostate carcinoma cell line," Vet Comp Oncol, Mar. 2007, vol. 5(1), pp. 47-58.
Baker et al., "Inoculum standardization in antimicrobial susceptibility testing: evaluation of overnight agar cultures and the Rapid Inoculum Standardization System," J Clin Microbiol., Mar. 1983, vol. 17(3) pp. 450-457.
Benzaken et al., "Diagnosis of gonococcal infection in high risk women using a rapid test," Sex Transm Infect, Dec. 2006, vol. 82(Suppl V), pp. v26-v28.
Biddle et al., "Disc agar diffusion antimicrobial susceptibility tests with β-lactamase producing Neisseria gonorrhoeae," J. Antibiotics, Apr. 1978, vol. 3, pp. 352-358.
Booth et al., "OSU-03012 and Viagra Treatment Inhibits the Activity of Multiple Chaperone Proteins and Disrupts the Blood-Brain Barrier: Implications for Anti-Cancer Therapies," J Cell Physiol, Aug. 2015, vol. 230(8), pp. 1982-1998.
Camara et al., "Molecular characterization of two high-level ceftriaxone-resistant Neisseria gonorrhoeae isolates detected in Catalonia, Spain", J. Antimicrob. Chemother., May 7, 2012, vol. 67(8), pp. 1858-1860.
Caron et al., "Activated forms of H-RAS and K-RAS differentially regulate membrane association of PI3K, PDK-1, and AKT and the effect of therapeutic kinase inhibitors on cell survival," Mol Cancer Ther, Feb. 2005, vol. 4(2), pp. 257-270.
Cen et al., "PDK-1/AKT pathway as a novel therapeutic target in rhabdomyosarcoma cells using OSU-03012 compound," Br J Cancer, Sep. 11, 2007, vol. 97(6), pp. 785-791.
Centers for Disease Control and Prevention (CDC), "Antibiotic resistance threats in the United States," 2013. http://www.cdc.gov/drugresistance/threat-report-2013/.
Centers for Disease Control and Prevention (CDC), "Gonorrhea—CDC fact sheet (detailed version)," 2014. http://www.cdc.gov/std/gonorrhea/STDFact-gonorrhea-detailed.htm.
Chiu et al., "Eradication of intracellular Francisella tularensis in THP-1 human macrophages with a novel autophagy inducing agent," J. Biomed. Sci., Dec. 9, 2009, vol. 16(110), pp. 1-10.
Chiu et al., "Eradication of intracellular *Salmonella enterica* serovar typhimurium with a smallmolecule, host cell-directed agent," Antimicrob. Agents Chemother, Dec. 2009, vol. 53(12), pp. 5236-5244.
Clinical and Laboratory Standards Institute (CLSI), "Performance Standards for Antimicrobial Susceptibility Testing; Twenty-Fourth Informational Supplement," Jan. 2014, vol. 34(1), ISBN 1-56238-898-3.

(Continued)

*Primary Examiner* — Leslie A. Royds Draper
(74) *Attorney, Agent, or Firm* — Potomac Law Group, PLLC; Jeremy A. Cubert, Esq.

(57) ABSTRACT

Compositions and methods for preventing and treating *Neisseria gonorrhoeae* infection with AR-12 alone or in combination with antibiotics are provided.

13 Claims, 3 Drawing Sheets

(56) References Cited

OTHER PUBLICATIONS

Edwards et al., "A co-operative interaction between Neisseria gonorrhoeae and complement receptor 3 mediates infection of primary cervical epithelial cells," Cell. Microbiol., Sep. 2002, vol. 4(9), pp. 571-584.
Edwards et al., "Gonococcal Phospholipase D Modulates the Expression and Function of Complement Receptor 3 in Primary Cervical Epithelial Cells," Infect Immun., Nov. 2003, vol. 71(11), pp. 6381-6391.
Edwards et al., "Neisseria gonorrhoeae PLD directly interacts with Akt kinase upon infection of primary, human, cervical epithelial cells," Cell. Microbiol., Aug. 2006, vol. 8(8), pp. 1253-1271.
Edwards et al., "Neisseria gonorrhoeae survival during primary, human, cervical epithelial cell infection requires nitric oxide and is augmented by progesterone," Infect. Immun., Mar. 2010, vol. 78(3), pp. 1202-1213.
Edwards et al., "The role of complement receptor 3 (CR3) in Neisseria gonorrhoeae infection of human cervical epithelia," Cell. Microbiol., Sep. 2001, vol. 3(9), pp. 611-622.
Edwards et al., "The role of lipooligosaccharide in Neisseria gonorrhoeae pathogenesis of cervical epithelia: lipid A serves as a C3 acceptor molecule," Cell. Microbiol., Sep. 2002, vol. 4(9), pp. 585-598.
Elmros et al., "Autolysis of Neisseria gonorrhoeae," J Bacteriol., May 1976, vol. 126(2), pp. 969-976.
Hussain et al., "Investigation of the complement receptor 3 (CD11b/CD18) in human rectal epithelium," Clin Exp Immunol., Nov. 1995, vol. 102(2), pp. 384-388.
International Preliminary Report on Patentability issued in International Patent Application No. PCT/US2016/053843 dated Apr. 3, 2018.
Ison et al., "Gonorrhoea treatment failures to cefixime and azithromycin in England, 2010," Euro. Surveill., Apr. 7, 2011, vol. 16(14), pp. 1-4.
Jennings et al., "Neisseria gonorrhoeae pilin glycan contributes to CR3 activation during challenge of primary cervical epithelial cells," Cell Microbiol, Jun. 2011, vol. 13(6), pp. 885-896.
Kim et al., "Anti-gastric cancer effects of celecoxib, a selective COX-2 inhibitor, through inhibition of Akt signaling," J Gastroenterol Hepatol, Mar. 2009, vol. 24(3), pp. 480-487.
Kucab et al., "Celecoxib analogues disrupt Akt signaling, which is commonly activated in primary breast tumours," Breast Cancer Res, Aug. 1, 2005, vol. 7, pp. R796-R807.
Mateo et al., "A first-inhuman phase I trial of AR-12, a PDK-1 inhibitor, in patients with advanced solid tumors," J Clin Oncol., May 20, 2013. vol. 31(25), p. 2608.
NIAID, "Two New Promising Treatment Regimens for Gonorrhea, Additional Options Urgently Needed," Jul. 15, 2013, National Center for HIV/AIDS Viral Hepatitis, NIH News. http://www.niaid.nih.gov/news/newsreleases/2013/Pages/GonorrheaTrial.aspx.
Ohnishi et al., "Is Neisseria gonorrhoeae initiating a future era of untreatable gonorrhea?: Detailed characterization of the first strain with high-level resistance to ceftriaxone," Antimicrob. Agents Chemother., Jul. 2011, vol. 55(7), pp. 3538-3545.
Ostberg et al., "Conserved regions of gonococcal TbpB are critical for surface exposure and transferrin iron utilization," Infect Immun, Sep. 2013, vol. 81(9), pp. 3442-3450.
Peeling et al., "Rapid tests for sexually transmitted infections (STIs): the way forward," Sex Transm Infect, Dec. 2006, vol. 82(Suppl V), pp. v1-v6.
Porchia et al., "2-amino-N-{4-[5-(2-phenanthrenyl)-3-(trifluoromethyl)-1Hpyrazol-1-yl]-phenyl} acetamide (OSU-03012), a celecoxib derivative, directly targets p21-activated kinase," Mol Pharmacol., Nov. 2007, vol. 72(5), pp. 1124-1131.
Romoren et al., "Chlamydia and gonorrhoea in pregnant Batswana women: time to discard the syndromic approach?," BMC Infect Did, Apr. 16, 2007, vol. 7(27), pp. 1-11.
Spence et al., "Laboratory Maintenance of Neisseria gonorrhoeae," Curr Protoc Microbiol., Feb. 2008, pp. 4A.1.1-4A.1.26.
Tapsall et al., "Two cases of failed ceftriaxone treatment in pharyngeal gonorrhea verified by molecular microbiological methods," J. Med. Microbiol., May 2009, vol. 58(Pt 5), pp. 683-687.
Timmerman et al., "Ultrastructural analysis of the pathogenesis of Neisseria gonorrhoeae endometrial infection," Cellular Microbiology, May 2005, vol. 7(5), pp. 627-636.
Unemo et al., "Ceftriaxone treatment failure of pharyngeal gonorrhoea verified by international recommendations, Sweden, Jul. 2010," Euro. Surveill., Feb. 10, 2011, vol. 16(6), pp. 1-3, PII 19792.
Unemo et al., "First Neisseria gonorrhoeae strain with resistance to cefixime causing gonorrhoea treatment failure in Austria, 2011," Euro. Surveill., Oct. 27, 2011, vol. 16(43), pp. 1-3, PII 19998.
Unemo et al., "Highlevel cefixime and ceftriaxone-resistant N. gonorrhoeae in France: novel penA mosaic allele in a successful international clone causes treatment failure," Antimicrob. Agents Chemother., Mar. 2012, vol. 56(3), pp. 1273-1280.
Unemo et al., "Treatment failure of pharyngeal gonorrhoea with internationally recommended first-line ceftriaxone verified in Slovenia, Sep. 2011," Euro. Surveill., Jun. 21, 2012, vol. 17(25), pp. 1-4.
Unemo et al., "Two cases of verified clinical failures using internationally recommended first-line cefixime for gonorrhea treatment, Norway, 2010." Euro. Surveill., Nov. 25, 2010, vol. 15(47), pp. 1-3, PII 19721.
Wade et al., "A fully defined, clear and protein-free liquid medium permitting dense growth of Neisseria gonorrhoeae from very low inocula," FEMS Microbiol Lett., Aug. 2007, vol. 273(1), pp. 35-37.
Wang et al., "Targeting endoplasmic reticulum stress and Akt with OSU-03012 and gefitinib or erlotinib to overcome resistance to epidermal growth factor receptor inhibitors," Cancer Res., Apr. 15, 2008, vol. 68(8), pp. 2820-2830.
World Health Organization, Department of Reproductive Health and Research, "Global action plan to control the spread and impact of antimicrobial resistance in Neisseria gonorrhoeae," 2012, ISBN 978-92-4-150350-1. http://www.who.int/reproductivehealth/publications/rtis/9789241503501/en/.
Written Opinion issued in International Patent Application No. PCT/US2016/053843 dated Jan. 13, 2017.
Zhang et al., "OSU-03012, a novel celecoxib derivative, is cytotoxic to myeloma cells and acts through multiple mechanisms," Clin Cancer Res, Aug. 2007, vol. 13(16), pp. 4750-4758.
Zhu et al., "From the cyclooxygenase-2 inhibitor celecoxib to a novel class of 3-phosphoinositide-dependent protein kinase-1 inhibitors," Cancer Res., Jun. 15, 2004, vol. 64(12), pp. 4309-4318.

\* cited by examiner

COMPOSITIONS AND METHODS FOR INHIBITING THE GROWTH OF NEISSERIA GONORRHOEAE

PRIORITY CLAIM

This application claims priority to U.S. Provisional Patent Application Ser. No. 62/233,723 filed on Sep. 28, 2015. The above referenced provisional patent application is incorporated herein by reference as if restated in full. All references cited herein, including, but not limited to patents and patent applications, are incorporated by reference in their entirety.

All references cited herein, including but not limited to patents and patent applications, are incorporated by reference in their entirety

BACKGROUND

In the United States, *Neisseria gonorrhoeae* (also know as Ng, the gonococcus) infections are the second most common notifiable infectious disease, with annual associated health costs exceeding one billion dollars. An estimated 106 million new cases occur globally each year (1), and greater than 800,000 cases occurred in the United States in 2012 (2, 3). The reported number of cases of antibiotic resistant Ng strains is increasing, further complicating the treatment efforts of this transmittable disease. Thus, the continued prevalence of Ng, and its associated morbidity support an urgent need for continued efforts to develop and implement novel Ng diagnostics, therapeutics, and vaccines.

Gonococcal vaccine development has proven to be exceptionally difficult. This is alarming in view of the increasing global prevalence of multidrug resistant (MDR) Ng, with increasing reports of treatment failures, and the recent emergence of untreatable MDR Ng strains (4-12). In 2013, the Center's for Disease Control (CDC) announced that Ng was one of three bacteria that represented an urgent threat with regard to increasing antibiotic-resistance (13). MDR Ng is of particular concern in developing countries, which are heavily impacted by gonococcal diseases and where diagnosis and treatment rely heavily upon a syndromic approach (i. e., the treatment of all at risk patients based upon the presence of symptoms rather than a definitive diagnosis) (14-16). The global medical community's management of Ng further contributes to antibiotic-resistance by the overuse and misuse of antibiotics (14-16). Thus, there is an urgent need for the identification of novel therapeutics that can be rapidly translated into clinical use and for which the gonococcus is unlikely to develop resistance.

AR-12 (previously known as OSU-03012) is a celecoxib derivative that was discovered at The Ohio State University. The compound was initially developed in the oncology setting and a phase I study demonstrated an acceptable safety profile with long-term oral exposures up to 33 weeks. The AR-12 oncology dose most likely substantially exceeds the exposure needed in the infectious disease setting. AR-12 (a.k.a. OSU-03012) has been previously shown to exhibit anti-tumor and anti-bacterial activity. It is thought that AR-12 induces autophagy of cells harboring intracellular bacteria. Supportive preclinical studies demonstrated that AR-12 has rapid blood brain barrier penetration and appreciable accumulation in tissues, exceeding the blood level concentrations several fold. (36).

AR-12 was initially developed by Arno Therapeutics (Arno) in 2008 for an oncology indication. In support of this oncology program, Arno initiated an Investigational New Drug (IND) enabling toxicology program, which included standard Good Laboratory Practice (GLP) tests (e. g. genotoxicity), a battery of safety pharmacology studies, and 28-day general toxicity assessments performed in rats and dogs. Before Arno's involvement, the National Cancer Institute had generated preclinical ADME (i. e., absorption, distribution, metabolism, and excretion) and toxicology data in the mouse model as part of the Rapid Access to Intervention Development (RAID) program. AR-12 synthesis was optimized and scaled-up to approximately 50 kg (purity >99.5%; stability ≥24 months at ambient conditions) under Current Good Manufacturing Practices (cGMP) conditions in anticipation of continued clinical development in the oncology setting.

AR-12 was originally investigated in a Phase I oncology study (27), an IND (IND #103799) was previously filed with the Food and Drug Administration (FDA), and an Investigational Medicinal Product Dossier (IMPD) was filed with the Medicines and Healthcare Products Regulatory Agency (MHRA Reference: 35725/0001/001-0001 [EudraCT Number: 2009-014285-25]) in the United Kingdom, which enabled the Phase I study entitled: "A Phase I Study of AR-12 (2-Amino-N-[4-[5-(2-phenanthrenyl)-3-(trifluoromethyl)-1H-pyrazol-1-yl]phenyl]-acetamide) in Adult Patients With Advanced or Recurrent Solid Tumors or Lymphoma, for Which No Standard Therapy Is Available". At doses appropriate in the oncology setting, the dose limiting toxicities (DLT) included: fatigue, dizziness, and skin rash. Thirty-five patients were enrolled at nine dose levels. With the original formulation tested, the recommended oncology Phase II dose was 800 mg twice daily. It is anticipated that the doses required in the infectious disease setting will be significantly below the doses required in the oncology arena, based on various preclinical studies in multiple pathogens.

Pharmacokinetic data from this Phase I study show that high blood levels of AR-12 can be obtained using on oral dosage form. The half-life in humans is long and is estimated to be approximately 60 hours. Early preclinical studies in the mouse model show that AR-12 permeates into tissues and tissue concentrations can significantly exceed blood levels. This is a favorable property for the treatment of Ng, which is, with rare exception, a mucosal pathogen. AR-12 is slowly released from the tissue back into the bloodstream and slowly excreted, which explains its long half-life.

SUMMARY

In one aspect, the celecoxib derivative, AR-12, functions as a novel anti-gonococcal therapeutic agent using human, primary cell models of infection. In another aspect, methods described herein are directed predominately through the human host, not the bacterium itself (18, 19).

As described herein, AR-12 has antimicrobial activity against the MDR Ng strain, WHO-M. Distinct from traditional antimicrobial strategies, our data demonstrates that AR-12 exerts its antimicrobial activity in a human infection model. Combating gonococcal disease by targeting the human pathways required for Ng invasion and intracellular survival represents a novel therapeutic strategy that has not been explored with regard to Ng. This unique approach is not impacted by gonococcal MDR mechanisms and, moreover, may (additively or synergistically) provide opportunities to combine with existing anti-Ng therapies and/or complement the human innate immune clearance mechanisms.

Aspects described herein provide methods of reducing the titer of *Neisseria gonorrhoeae* in a human infected with *Neisseria gonorrhoeae* by administering AR-12 to the infected human in an amount sufficient to reduce the amount of viable *Neisseria gonorrhoeae* in the infected human by about 300-fold (which represents a 3-log reduction in colony forming units (CFUs)) after about 6 hours compared to an untreated human infected with *Neisseria gonorrhoeae*. In another aspect, AR-12 is administered to the infected human in an amount sufficient to reduce the amount of viable *Neisseria gonorrhoeae* in the infected human by at least about 600-fold (which represents a 6-log reduction, with no viable bacteria detected) after about 24 hours compared to an untreated infected human.

In another aspect, the amount of AR-12 administered to the infected mammal in an amount sufficient to achieve a blood or tissue concentration of at least about 1 to 12 µM. In one aspect, the amount sufficient to achieve a blood or tissue concentration of at least about 1 to 12 µM is about 10 to 1600 mg once or twice daily. In yet another aspect, the amount of AR-12 administered to the infected mammal is sufficient to achieve a blood or tissue concentration of at least about 10 µM.

BRIEF DESCRIPTION OF THE DRAWINGS

The feature and nature of the present disclosure will become more apparent from the detailed description set forth below when taken in conjunction with the accompanying drawings.

DETAILED DESCRIPTION

The disclosed methods, compositions, and devices below may be described both generally as well as specifically. It should be noted that when the description is specific to an aspect, that aspect should in no way limit the scope of the methods.

As used herein, the term "AR-12" refers to ($C_{26}H_{19}F_3N_4O$ and 2-amino-N-(4-(5-(phenanthren-2-yl)-3-(trifluoromethyl)-1H-pyrazol-1-yl)phenyl)acetamide)) having the following structure:

The term "AR-12" also includes, for example, analogs of AR-12 (e.g., the compounds described in U.S. Pat. Nos. 7,576,116, 8,546,441, 8,541,460, 8,039,502, and 8,080,574, hereby incorporated by reference in their entirety).

Aspects described herein provide methods of reducing the titer of *Neisseria gonorrhoeae* in a human infected with *Neisseria gonorrhoeae* by administering AR-12 to the infected human in an amount sufficient to reduce the amount of viable *Neisseria gonorrhoeae* in the infected human by about 3-log after about 6 hours compared to an untreated human infected with *Neisseria gonorrhoeae*. In another aspect, AR-12 is administered to the infected human in an amount sufficient to reduce the amount of viable *Neisseria gonorrhoeae* in the infected human by at least about 7-log after about 24 hours compared to an untreated infected human.

In another aspect, the amount of AR-12 administered to the infected mammal in an amount sufficient to achieve a blood or tissue concentration of at least about 1 to 12 µM. In one aspect, the amount sufficient to achieve a blood or tissue concentration of at least about 1 to 12 µM is about 10 to 1600 mg once or twice daily. In yet another aspect, the amount of AR-12 administered to the infected mammal is sufficient to achieve a blood or tissue concentration of at least about 10 µM.

In another aspect, AR-12 is administered to infected mucosal tissue (e.g., urethral, vaginal, cervical, rectal, conjunctival, and pharyngeal). In a further aspect, AR-12 contacts the infected mucosal tissue from about 3 to about 24 hours. In yet another aspect, AR-12 contacts the infected mucosal tissue for at least about 3 hours.

In another aspect, the described methods further comprise administering an antibiotic to the infected human (e.g., ceftriaxone and gentamicin). The antibiotic can be provided in an amount to achieve blood or tissue concentrations from about 5 µg/ml to about 100 µg/ml.

As used herein, the term "administer" or "administered" refers to applying, ingesting, inhaling or injecting, or prescribing an active ingredient to treat a host or patient in need of treatment. In one aspect, the host is a human.

An "untreated host" is a host that has not received AR-12 or another antimicrobial treatment. In this aspect, AR-12 can be administered by the patient, a healthcare professional, a caretaker, and also includes prescribing or dispensing the compositions described herein to the patient.

The terms "treat," "reduce," "suppress," "inhibit," "prevent," or similar terms, as used herein, do not necessarily mean 100% or complete treatment or prevention. Rather, these terms refer to various degrees of treatment or prevention of a particular disease (e.g., 100%, 90%, 80%, 70%, 60%, 50%, 40%, 30%, 20%, 10%, 5%, or 1%) as recognized in the art as being beneficial.

The terms "treatment" or "prevention" also refer to delaying onset of a disease for a period of time or delaying onset indefinitely. The term "treatment" or "treating" refers to administering a drug or treatment to a patient or prescribing a drug to a patient (e.g., by a doctor, nurse, or other medical professional) where the patient or a third party (e.g., caretaker, family member, or health care professional) administers the drug or treatment.

The term "amount effective" refers to an amount of a drug or treatment (e.g., AR-12, antibiotic) that will treat, reduce, suppress, inhibit, prevent disease(s) or condition(s) (e.g., Ng infection) or prolong survival of a mammal with a disease or condition.

The term "prolong" or "prolonging" as used herein, refers to increasing time of survival of a mammal receiving treatment compared to a mammal that does not receive treatment. In this aspect, "prolonged survival" can refer to increasing the lifespan of the mammal by, for example, 1%, 5%, 10%, 20%, 30%, 40%, 50%, 60%, 70%, 80% or 90% of the lifespan of mammal that does not have an Ng infection.

Humans are the only reservoir for Ng. Thus, in another aspect, methods described herein relate to the clinical relevance of the use of primary human mucosal epithelial cells. Tests described herein show the therapeutic potential of AR-12 under conditions mimicking the active human infectious environment (i.e., variable steroid hormone (SH) concentrations and low oxygen tensions).

Progesterone (Pg) augments gonococcal invasion of and survival within PEX cells. Clinical data indicate that there is a hormonal component to Ng infection in women. Pilot studies indicated that under conditions reflective of the Pg-predominant luteal phase of the female menstrual cycle, the ability of Ng to associate with and invade PEX cells is enhanced. Therefore, to more closely mimic the luteal phase of the menses cycle, when Pg concentrations fluctuate between 3 nM and 30 nM, the effect of Pg on Ng invasion of and survival within PEX cells was evaluated using a gentamicin-survival assays with 0.4 nM of estradiol (E2) and variable concentrations of Pg (FIG. 1)

Figure 1A:
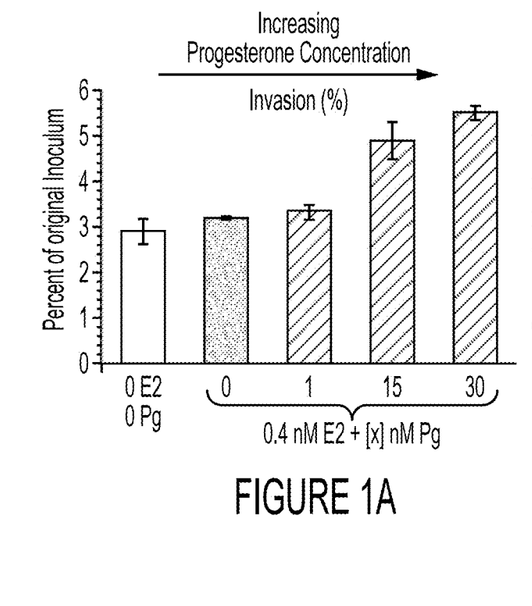
FIGS. 1A and 1B show an exemplary invasion assay (FIG. 1A) and survival assay (FIG. 1B) in Ng infected primary epithelial cells derived from the human cervix (PEX) cells treated with and without estradiol, progesterone, and an Akt inhibitor.

Gonococcal invasion increased with increasing concentrations of Pg, suggesting that Pg augments gonococcal invasion of and/or intracellular survival within PEX cells (FIG. 1A). Further studies were conducted to determine if Pg augmented the ability of gonococci to survive intracellularly within PEX cells. Following gentamicin treatment (to kill extracellular bacteria), infected cell monolayers were either lysed (releasing the invasive Ng) and serial dilutions were plated, or they were re-incubated in antibiotic free medium for 1 or 3 hours longer before plating the PEX cell lysate and quantitating colony forming units. Akt inhibitor VII was included or omitted from these experiments.

Figure 1B:
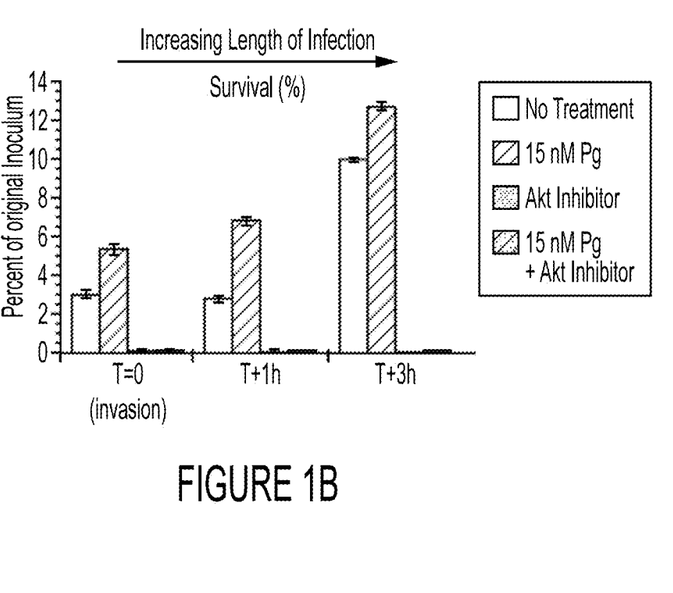

In the absence of Pg, there was no significant difference in the ability of wildtype bacteria to survive one hour after they had invaded PEX cells; however, by 3 hours post-invasion this number had more than doubled (FIG. 1B). The ability of gonococci to invade, as well as survive within, PEX cells was enhanced by the presence of Pg (FIG. 1B).

An established body of evidence demonstrates that AR-12 (OSU-03012) is an inducer of host effector cell autophagy, thus, potentiating the cellular immune response. AR-12 is known to inhibit GRP78 (also known as BiP, HSPA5) that results in the up-regulation of PERK, which induces the formation of autophagosomes and, subsequently, host cell autophagy. AR-12 also down regulates the chaperone proteins HSP70 and HSP90. AR-12 may also have activity with respect to Akt inhibition. In one aspect, Akt inhibition severely impaired the ability of gonococci to invade PEX cells, which could not be rescued by Pg (FIG. 1B). Collectively, these data suggest that Pg functions upstream, or at the level, of Akt activation to promote the intracellular survival of Ng during cervical infection.

Modified gentamicin survival assays were performed in which pex cells were challenged with our preferred laboratory Ng strain, 1291, or the MDR Ng strain, WHO-M (beta-lactam-, ciprofloxacin-, and rifampicin-resistant; plus a mtrR mutation that could effect resistance to other compounds (35)). Infections were allowed to proceed for 90 min to allow Ng to adhere to and invade PEX cells. Vehicle control, AR-12, ceftriaxone, or gentamicin was then added to established infections.

Figure 2A:
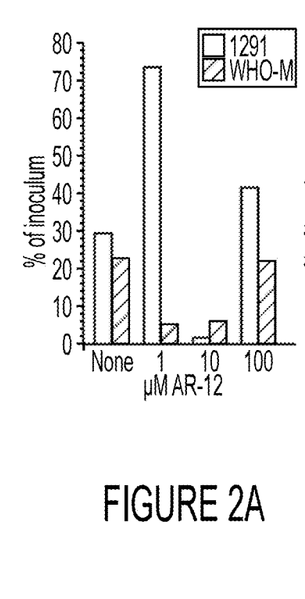
FIGS. 2A-2E provide the results of an exemplary survival assay showing the antimicrobial effects of AR-12 towards Ng strains 1291 and (MDR) WHO-M at 3 hours (FIG. 2A), 6 hours (FIG. 2B), and 24 hours (FIG. 2C), with ceftriaxone and gentamicin (24 hours) used as controls (FIG. 2D); and an exemplary assay showing the reduction in colony forming units (CFU) of Ng strains 1291 and WHO-M after treatment with AR-12 or ceftriaxone measured 6 hours or 24 hours post treatment of an established human cervical cell infection (FIG. 2E).

At the indicated times post-challenge, the infection medium was removed, the PEX cell monolayers were rinsed and lysed, and viable Ng were enumerated by counting CFUs after plating serial dilutions of the PEX cell lysates. The percentage of Ng that survived the test treatment was determined as a function of the infection inoculum. In this aspect, the units are colony forming units—percent survival calculated as: [(#CFU (x dilution factor)) divided by (number of bacteria used as the infection inoculum (~typically $1\times10^7$ bacteria per ml))×100]. A significant reduction (at least about 300 fold) in viable Ng was observed following a 3-hour incubation with 10 µM AR-12 (FIG. 2A). Further reductions in the number of viable Ng (FIG. 2B) (at least about 600 fold) were achieved by extending the length of time (6 h) for AR-12 treatment of Ng-infected PEX cells, and no viable Ng were recovered after 24 h with 10 µM AR-12 (FIG. 2C) resulted in a further reduction.

Figure 2B:
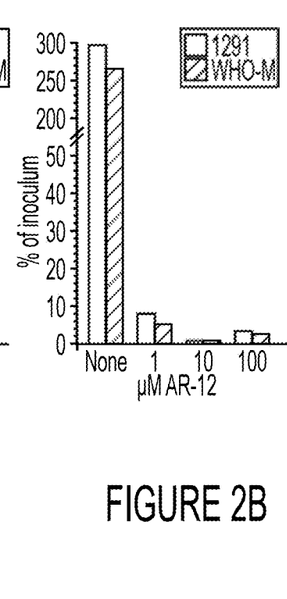
Figure 2C:
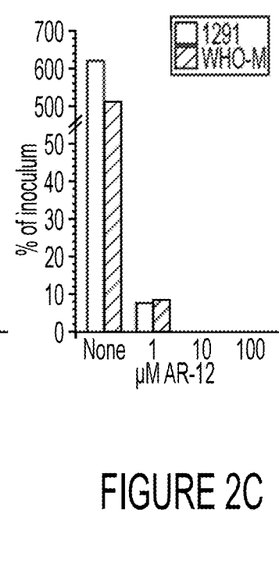
Figure 2D:
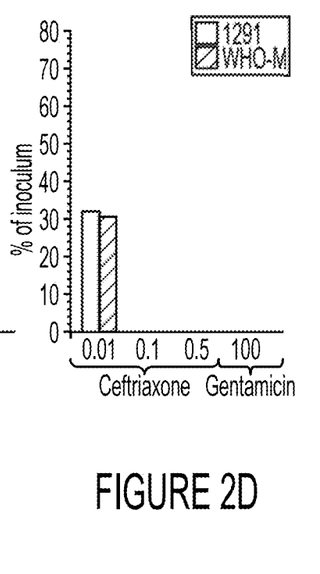
Figure 2E:
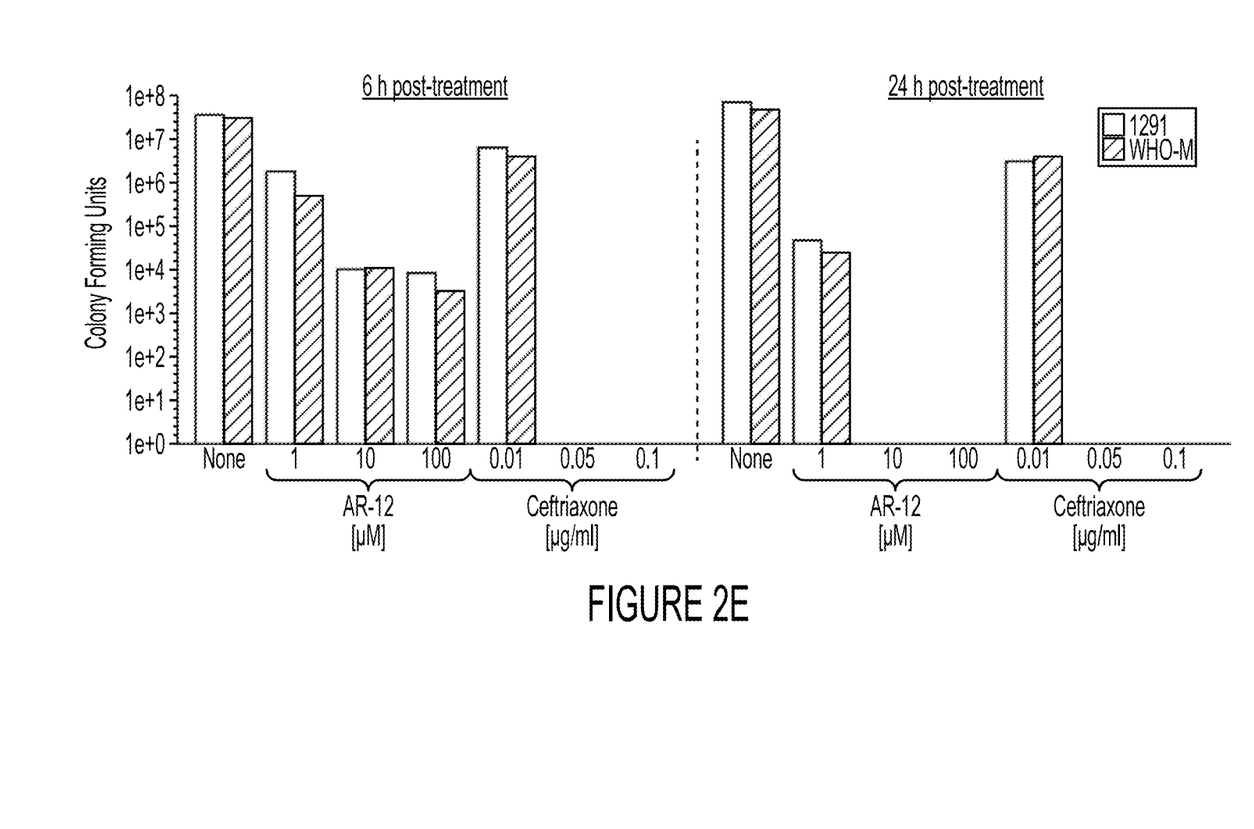

As shown in FIGS. 2A-2E, modified gentamicin survival assays demonstrate that AR-12 exhibits antimicrobial activity towards Ng strains 1291 (red) and (MDR) WHO-M (blue) (FIG. 2A (3 hours); FIG. 2B (6 hours); and FIG. 2C (24 hours post-AR-12 addition to established human cervical cell infections). FIG. 2D provides ceftriaxone and gentamicin (24 hours) assay controls in µg/ml. In FIGS. 2A-2D, data are shown as the percentage of the infection inoculum that survive drug treatment (y-axis). FIG. 2E provides actual bacterial numbers, as colony forming units, at 6 and 24 hours post-drug addition. FIG. 2E shows that 10 µm AR-12 reduced the amount of viable Ng in the infected human by at least about 3-log after about 6 hours and by at least about 7-log after about 24 hours compared to an untreated infection. Concentrations of AR-12 tested are shown on the x-axis. "None" refers to vehicle control.

Thus, AR-12 has a bactericidal effect with 100% killing of Ng, and no spontaneous resistance to AR-12 observed by 24 hours post-AR-12 treatment. This effect was specific to infection of human cells in that AR-12 was not effective against the Ng by antimicrobial disk diffusion assays, which prohibit Ng growth on agar plates.

In one aspect, taken together, the above data show that AR-12, a small molecule, can be used to treat MDR Ng.

In another aspect, AR-12 or the compositions described herein can be used to treat or prevent the illness and/or disease caused by wild-type NG and multi-drug resistant NG. AR-12 can be provided to an infected patient concurrently with an antibiotic or serially in any suitable order. In another aspect, AR-12 and the antibiotic can be administered to patients simultaneously or AR-12 and the antibiotic can be formulated together.

The compositions described herein can be administered orally, parenterally (IV, IM, depot-IM, SQ, and depot-SQ), sublingually, intranasally, inhalation, intrathecally, conjunctival, topically, vaginally, rectally, or administered into the urethra. Dosage forms known to those of skill in the art are suitable for delivery of the compositions described herein.

AR-12 can be formulated into suitable pharmaceutical preparations such as creams, gels, eye drops, suspensions, tablets or suppositories for topical, vaginal, rectal, urethral or mucosal applications and administration; tablets, capsules, suspensions, elixirs for oral administration; and inhalers for administration into the lungs and airways or in sterile solutions or suspensions for parenteral administration. AR-12 can be formulated into pharmaceutical compositions using techniques and procedures well known in the art.

In one aspect, about 10 to 1600 mg, about 5 to about 200 mg, or about 10 to about 50 mg of the AR-12, or a physiologically acceptable salt or ester can be compounded with a physiologically acceptable vehicle, carrier, excipient, binder, preservative, pain reliever, stabilizer, flavor, etc., in a unit dosage form as called for by accepted pharmaceutical practice. The amount of active substance in compositions or preparations comprising AR-12 is such that a suitable dosage achieving the therapeutic range indicated is obtained.

In another aspect, the compositions can be formulated in a unit dosage form, each dosage containing from about 1 to about 1000 mg, about 1 to about 500 mg, or about 10 to about 200 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

In one aspect, one or more of AR-12 is mixed with a suitable pharmaceutically acceptable carrier to form compositions. Upon mixing or addition of the compound(s), the resulting mixture may be a cream, suppository, tablet, solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. In one aspect, the effective concentration is sufficient for lessening or ameliorating at least one symptom of the disease, disorder, or condition treated and may be empirically determined.

Pharmaceutical carriers or vehicles suitable for administration of AR-12 described herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

In another aspect, if AR-12 exhibits insufficient solubility in water, methods for solubilizing may be used. Such methods are known and include, but are not limited to, using co-solvents such as dimethylsulfoxide (DMSO), using surfactants (e.g., TWEEN, poloxamer) and dissolution in aqueous sodium bicarbonate. Micronization, reduction of particle size to nanoparticles and co-crystallization may also be used in formulating effective pharmaceutical compositions. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

In another aspect, AR-12 as described herein may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

In another aspect, AR-12 and compositions described herein can be enclosed in multiple or single dose containers. The enclosed compounds and compositions can be provided in kits, for example, including component parts that can be assembled for use. For example, AR-12 in lyophilized form and a suitable diluent may be provided as separated components for combination prior to use. A kit may include AR-12 and a second therapeutic agent for co-administration. AR-12 and second therapeutic agent may be provided as separate component parts. A kit may include a plurality of containers, each container holding one or more unit dose of AR-12 described herein. In one aspect, the containers can be adapted for the desired mode of administration, including, but not limited to suspensions, tablets, gel capsules, sustained-release capsules, and the like for oral administration; depot products, pre-filled syringes, ampoules, vials, and the like for parenteral administration; and patches, medipads, gels, suspensions, suppositories, creams, eye drops and the like for topical, vaginal, rectal, urethral, conjunctival or other mucosal applications and administration.

The concentration of AR-12 in the pharmaceutical composition will depend on absorption, inactivation, and excretion rates of the active compound, the dosage schedule, and amount administered as well as other factors known to those of skill in the art.

In another aspect, the active ingredient may be administered at once, or may be divided into a number of smaller doses to be administered at intervals of time (e.g., 1, 2, 3, or 4 times daily). It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient (e.g., any suitable filler/bulking agent) such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed or co-administered with other active materials that do not impair the desired action, or with materials that supplement the desired action. AR-12 can be used, for example, in combination with an antibiotic, antiviral, antifungal, pain reliever, or a cosmetic.

In one aspect, solutions or suspensions used for parenteral, intradermal, subcutaneous, inhalation, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, alcohols, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropyleneglycol, ethanol, N-methylpyrrolidone, surfactants and mixtures thereof. Liposomal suspensions including tissue-targeted liposomes may also be suitable as pharmaceutically acceptable carriers. These may be prepared according to methods known in the art.

In one aspect, AR-12 can be formulated into suitable pharmaceutical preparations such as creams, gels, suspensions, tablets or suppositories for topical, vaginal, rectal, urethral or mucosal applications and administration. In this aspect, pharmaceutical preparations can include one or more of any of the following components: water, glycerin, polyethylene glycol polymers (PEG), mineral salts and mineral oxides, fixed oils of vegetable origin, hydrogenated oils of vegetable origin, hydrocarbons obtained from petroleum, fats obtained from animals, stearyl alcohol, esters of saturated fatty alcohols, emulsifying and suspending agents such as sodium lauryl sulfate, gelatin, polyvinyl alcohol; benzoic acid, oleic acid, and antimicrobial agents such as benzyl alcohol and methyl parabens. Buffers, preservatives, antioxidants, and the like can be incorporated as required. Suitable pharmaceutical preparations may contain penetration enhancers such as DMSO, azones, pyrrolidones, saturated fatty acids of an alkyl chain length of approximately C10-C12 with a polar head group, urea and the like as known to those skilled in the art. Topical preparations can be enclosed in single or multiple dose containers made of plastic or other suitable material.

In another aspect, AR-12 may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

In yet another aspect, compounds employed in the methods of the disclosure may be administered enterally or parenterally. When administered orally, compounds employed in the methods of the disclosure can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods described herein need to be administered only once or twice daily.

The dosage forms can be administered to the patient 1, 2, 3, or 4 times daily. AR-12 as described herein can be administered either four or fewer times, or even once or twice daily.

The terms "therapeutically effective amount" and "therapeutically effective period of time" are used to denote treatments at dosages and for periods of time effective to reduce microbial growth. As noted above, such administration can be parenteral, oral, sublingual, transdermal, topical, intranasal, or intrarectal. In one aspect, when administered systemically, the therapeutic composition can be administered at a sufficient dosage to attain a blood level of the compounds of from about 0.1 µM to about 20 µM. For localized administration, much lower concentrations than this can be effective, and much higher concentrations may be tolerated. One skilled in the art will appreciate that such therapeutic effect resulting in a lower effective concentration of AR-12 may vary considerably depending on the tissue, organ, or the particular animal or patient to be treated. It is also understood that while a patient may be started at one dose, that dose may be varied overtime as the patient's condition changes.

REFERENCES

1. World Health Organization, Department of Reproductive Health and Research 2012. Global action plan to control the spread and impact of antimicrobial resistance in *Neisseria gonorrhoeae*. http://www.who.int/reproductivehealth/publications/rtis/9789241503501/en/ISBN 978 92 4 150350 1.
2. NIAID, National Center for HIV/AIDS Viral Hepatitis 2013. Two New Promising Treatment Regimens for Gonorrhea, Additional Options Urgently Needed. NIH News. http://www.niaid.nih.gov/news/newsreleases/2013/Pages/GonorrheaTrial.aspx.
3. Centers for Disease Control and Prevention (CDC), Gonorrhea—CDC fact sheet (detailed version), 2014, http://www.cdc.gov/std/gonorrhea/STDFact-gonorrhea-detailed.htm.
4. Camara, J., J. Serra, J. Ayats, T. Bastida, D. Carnicer-Pont, A. Andreu, and C. Ardanuy (2012) Molecular characterization of two high-level ceftriaxone-resistant *Neisseria gonorrhoeae* isolates detected in Catalonia, Spain. J. Antimicrob. Chemother. 67:1858-1860.
5. Unemo, M., D. Golparian, R. Nicholas, M. Ohnishi, A. Gallay, and P. Sednaoui (2012) Highlevel cefixime and ceftriaxone-resistant *N. gonorrhoeae* in France: novel penA mosaic allele in a successful international clone causes treatment failure. Antimicrob. Agents Chemother. 56: 1273-1280.
6. Unemo, M., D. Golparian, M. Potocnik, and S. Jeverica (2012) Treatment failure of pharyngeal gonorrhoea with internationally recommended first-line ceftriaxone verified in Slovenia, September 2011. Euro. Surveill. 2012; 17(25):20200.
7. Ison, C. A., J. Hussey, K. N. Sankar, J. Evans, and S. Alexander (2011) Gonorrhoea treatment failures to 7. cefixime and azithromycin in England, 2010. Euro. Surveill. 2011; 16(14):pii=19833.
8. Ohnishi, M., D. Golparian, K. Shimuta, T. Saika, S. Hoshina, K. Iwasaki, S. Nakayama, J. Kitawaki, and M. Unemo (2011) Is *Neisseria gonorrhoeae* initiating a future era of untreatable gonorrhea?: Detailed characterization of the first strain with high-level resistance to ceftriaxone. Antimicrob. Agents Chemother. 55:3538-3545.
9. Unemo, M., D. Golparian, and A. Hestner (2011) Ceftriaxone treatment failure of pharyngeal gonorrhoea verified by international recommendations, Sweden, July 2010. Euro. Surveill. 2011; 16(6):19792.
10. Unemo, M., D. Golparian, A. Stary, and A. Eigentler (2011) First *Neisseria gonorrhoeae* strain with resistance to cefixime causing gonorrhoea treatment failure in Austria, 2011. Euro. Surveill. 16(43):19998.
11. Unemo, M., D. Golparian, G. Syversen, D. F. Vestrheim, and H. Moi (2010) Two cases of verified clinical failures using internationally recommended first-line cefixime for gonorrhea treatment, Norway, 2010. Euro. Surveill. 15(47):19721.
12. Tapsall, J., P. Read, C. Carmody, C. Bourne, S. Ray, A. Limnios, T. Sloots, and D. Whiley (2009) Two cases of failed ceftriaxone treatment in pharyngeal gonorrhoea verified by molecular microbiological methods. J. Med. Microbiol. 58(Pt 5):683-687.
13. Centers for Disease Control and Prevention (CDC) (2013) Antibiotic resistance threats in the United States, 2013. http://www.cdc.gov/drugresistance/threat-report-2013/
14. Romoren, M., J. Sundby, M. Velauthapillai, M. Rahman, E. Klouman, and P. Hjortdahl (2007) *Chlamydia* and gonorrhoea in pregnant Batswana women: time to discard the syndromic approach? BMC Infect Dis 7:27 doi:10.1186/1471-2334-7-27.
15. Benzaken, A. S., E. G. Galban, W. Antunes, J. C. Dutra, R. W. Peeling, D. Mambey, and A. Salama (2006) Diagnosis of gonococcal infection in high risk women using a rapid test. Sex Transm Infect 82(Suppl V):v26-v28.
16. Peeling, R. W., K. K. Holmes, D. Mabey, and A. Ronald (2006) Rapid tests for sexually transmitted infections (STIs): the way forward. Sex Transm Infect 82(Suppl V):v1-v6.
17. Zhu, J., J-W. Huang, P-H. Tseng, Y-T. Yang, J. Fowble, C-W. Shiau, Y-J. Shaw, S. K. Kulp, and C-S. Chen (2004) From the cyclooxygenase-2 inhibitor celecoxib to a novel class of 3-phosphoinositide-dependent protein kinase-1 inhibitors. Cancer Res. 64:4309-4318.
18) Chiu, H-C., S. K. Kulp, S. Soni, D. Wang, and J. S. Gunn, L. S. Schlesinger, and C-S. Chen (2009) Eradication of intracellular *Salmonella enterica* serovar typhimurium with a small molecule, host cell-directed agent. Antimicrob. Agents Chemother 53:5236-5244.
19. Chiu, H-C. S. Soni, S. K. Kulp, H. Curry, D. Wang, J. S. Gunn, L. S. Schlesinger, and C-S. Chen (2009) Eradication of intracellular *Francisella tularensis* in THP-1 human macrophages with a novel autophagy inducing agent. J. Biomed. Sci. 16:110 doi:10.1186/1423-0127-16-110.
20. Edwards, J. L. (2010) *Neisseria gonorrhoeae* survival during primary, human, cervical epithelial cell infection requires nitric oxide and is augmented by progesterone. Infect. Immun. 78:1202-1213.
21. Edwards, J. L. and M. A. Apicella (2006) *Neisseria gonorrhoeae* PLD directly interacts with Akt kinase upon infection of primary, human, cervical epithelial cells. Cell. Microbiol. 8:1253-1271.
22. Edwards, J. L., E. J. Brown, K. A. Ault, and M. A. Apicella (2001) The role of complement receptor 3 (CR3) in *Neisseria gonorrhoeae* infection of human cervical epithelia. Cell. Microbiol. 3:611-622.
23. Edwards, J. L., E. J. Brown, S. Uk-Nham, J. G. Cannon, M. S. Blake, and M. A. Apicella (2002) A cooperative interaction between *Neisseria gonorrhoeae* and complement receptor 3 mediates infection of primary cervical epithelial cells. Cell. Microbiol. 4: 571-584.
24. Edwards, J. L. and M. A. Apicella (2002) The role of lipooligosaccharide in *Neisseria gonorrhoeae* pathogenesis of cervical epithelia: lipid A serves as a C3 acceptor molecule. Cell. Microbiol. 4: 584-598.
25. Jennings, M. P., F. Jen, L. Roddam, M. A. Apicella, and J. L. Edwards (2011) Pilin glycosylation modulates CR3-mediated *Neisseria gonorrhoeae* infection of primary, human, cervical epithelial cells. Cell Microbiol 13:885-896.
26. Booth, L., J. L. Roberts, D. R. Cash, S. Tavallai, S. Jean, A. Fidanza, T. Cruz-Luna, P. Siembiba, K. A. Cycon, C. N. Cornelissen, and P. Dent (2015) GRP78/BiP/HSPA5/Dna K is a universal target for human disease. J Cell Physiol. 230:1661-1676.
27. Mateo, J., J. S. De Bono, R. K. Ramanathan, M. B. Lustberg, A. Zivi, D. Basset, M. Ng, A-M. Young, M. Garrett, S. Decordova, F. I. Raynaud, T. A. Yap, A. A. Zukiwski, S. Proniuk, and C. L. Shapiro (2013) A first-inhuman phase I trial of AR-12, a PDK-1 inhibitor, in patients with advanced solid tumors. J Clin Oncol. 31 (suppl; abstr 2608).
28. Caron, R. W., A. Yacoub, M. Li, X. Zhu, C. Mitchell, Y. Hong, W. Hawkins, T. Sasazuki, S. Shirasawa, A. P. Kozikowski, P. A. Dennis, M. P. Hagan, S. Grant, and P. Dent (2005) Activated forms of H-RAS and K-RAS differentially regulate membrane association of PI3K, PDK-1, and AKT and the effect of therapeutic kinase inhibitors on cell survival. Mol Cancer Ther 4: 257-270.
29. Kucab, J. E., C. Lee, C-S. Chen, J. Zhu, C. B. Gilks, M. Cheang, D. Huntsman, E. Yorida, J. Emerman, M. Pollak, and S. E. Dunn (2005) Celecoxib analogues disrupt Akt signaling, which is commonly activated in primary breast tumours. Breast Cancer Res 7:R796-R807.
30. Cen, L., F-C. Hsieh, H-J. Lin, C-S. Chen, S. J. Qualman, and J. Lin (2007) PDK-1/AKT pathway as a novel therapeutic target in rhabdomyosarcoma cells using OSU-03012 compound. Br J Cancer 97:785-791.
31. Porchia, L. M., M. Guerra, Y. C. Wang, Y. Zhang, A. V. Espinosa, M. Shinohara, S. K. Kulp, L. S. Kirschner, M. Saji, C. S. Chen, and M. D. Ringel (2007) 2-amino-N-{4-[5-(2-phenanthrenyl)-3-(trifluoromethyl)-1Hpyrazol-1-yl]-phenyl} acetamide (OSU-03012), a celecoxib derivative, directly targets p21-activated kinase. Mol Pharmacol. 72:1124-1131.
32. Alvarez, F. J., S. Murahari, C. G. Couto, T. J. Rosol, S. K. Kulp, C.-S. Chen, and W. C. Kisseberth (2007) 3-Phosphoinositide-dependent protein kinase-1/Akt signaling and inhibition in a canine prostate carcinoma cell line. Vet Comp Oncol 5:47-58.
33. Zhang, S., A. Suvannasankha, C. Crean, V. L. White, A. Johnson, C-S. Chen, and S. S. Farag (2007) OSU-03012, a novel celecoxib derivative, is cytotoxic to myeloma cells and acts through multiple mechanisms. Clin Cancer Res 2007; 13(16). doi:10.1158/1078-0432.CCR-07-0136.

34. Wang, Y-C., S. K. Kulp, D. Wang, C-C. Yang, A. M. Sargeant, J-H. Hung, Y. Kashida, M. Yamaguchi, G-D. Chang, and C-S. Chen (2008) Targeting endoplasmic reticulum stress and Akt with OSU-03012 and gefitinib or erlotinib to overcome resistance to epidermal growth factor receptor inhibitors. Cancer Res. 68:2820-2830.
35. Kim, N., C. H. Kim, D-W. Ahn, K. S. Lee, S-J. Cho, J. H. Park, M. K. Lee, J. S. Kim, H. C. Jung, and I. S. Song (2009) Anti-gastric cancer effects of celecoxib, a selective COX-2 inhibitor, through inhibition of Akt signaling. J Gastroenterol Hepatol 24:480-487.
36. Booth L, Roberts J L, Tavallai M, Nourbakhsh A, Chuckalovcak J, Carter J, Poklepovic A, Dent P. OSU-03012 and Viagra Treatment Inhibits the Activity of Multiple Chaperone Proteins and Disrupts the Blood-Brain Barrier: Implications for Anti-Cancer Therapies. J Cell Physiol. 2015 August; 230(8):1982-98. doi: 10.1002/jcp.24977. PubMed PMID: 25736380.

Not every element described herein is required. Indeed, a person of skill in the art will find numerous additional uses for and variations to the methods described herein, which the inventors intend to be limited only by the claims. All references cited herein are incorporated by reference in their entirety.

What is claimed is:

1. A method of reducing the amount of viable *Neisseria gonorrhoeae* in a human having a cervical epithelial cell infection with *Neisseria gonorrhoeae* comprising administering 2-amino-N-(4-(5-(phenanthren-2-yl)-3-(trifluoromethyl)-1H-pyrazol-2-yl)phenyl)acetamide (AR-12) to a human infected with *Neisseria gonorrhoeae*.

2. The method of claim 1, wherein the amount of AR-12 administered to the infected human is sufficient to achieve a blood or tissue concentration of at least about 1 to 12 µM.

3. The method of claim 2, wherein the amount of AR-12 administered to the infected human is sufficient to achieve a blood or tissue concentration of at least about 10 µM.

4. The method of claim 1, wherein AR-12 is administered to infected cervical tissue.

5. The method of claim 4, wherein AR-12 contacts the infected cervical tissue for at least about 3 hours.

6. The method of claim 5, wherein AR-12 contacts the infected cervical tissue from about 3 to about 24 hours.

7. The method of claim 1, further comprising administering an antibiotic to the infected human.

8. The method of claim 7, wherein the antibiotic is selected from the group consisting of ceftriaxone and gentamicin.

9. The method of claim 8, wherein the antibiotic is provided in an amount from about 5 µg/ml to about 100 µg/ml.

10. The method of claim 2, wherein the amount of AR-12 administered to the infected human is from about 10 to 1600 mg once or twice daily.

11. The method of claim 1, wherein AR-12 is administered in an amount from about 1 to about 1000 mg.

12. The method of claim 11, wherein the amount of AR-12 is from about 1 to about 500 mg.

13. The method of claim 11, wherein the amount of AR-12 is from about 10 to about 200 mg.

* * * * *

UNITED STATES PATENT AND TRADEMARK OFFICE
CERTIFICATE OF CORRECTION

PATENT NO. : 10,201,526 B2
APPLICATION NO. : 15/276739
DATED : February 12, 2019
INVENTOR(S) : Jennifer Edwards and Alexander Zukiwski Page 1 of 1

It is certified that error appears in the above-identified patent and that said Letters Patent is hereby corrected as shown below:

In the Specification

Column 1, Line 15 add the Government Support Clause:
--This invention was made with government support under grant number CA094829 awarded by National Institutes of Health and grant number DAMD17-02-1-0117 awarded by United States Army Medical Research and Materiel Command. The government has certain rights in the invention.--

Signed and Sealed this
Sixth Day of October, 2020

Andrei Iancu
*Director of the United States Patent and Trademark Office*